United States Patent [19]

Wootton

[11] 4,152,445

[45] May 1, 1979

[54] 1-(3-HYDROXYALK-1-YL)-5-(CARBOXYALK-YL)HYDANTOIN DERIVATIVES

[75] Inventor: Gordon Wootton, Sawbridgeworth, England

[73] Assignee: Beecham Group Limited, Great Britain

[21] Appl. No.: 915,165

[22] Filed: Jun. 14, 1978

Related U.S. Application Data

[63] Continuation-in-part of Ser. No. 858,562, Dec. 8, 1977, abandoned.

[30] Foreign Application Priority Data

Dec. 18, 1976 [GB] United Kingdom ............... 52955/76
Jul. 20, 1977 [GB] United Kingdom ............... 30369/77

[51] Int. Cl.² .................. A61K 31/415; C07D 233/78; C07D 233/86
[52] U.S. Cl. ................................. 424/273 R; 548/313
[58] Field of Search ...................... 548/313; 424/273 R

[56] References Cited

U.S. PATENT DOCUMENTS

| | | | |
|---|---|---|---|
| 2,290,281 | 7/1942 | Heuze .................................. | 548/313 |
| 2,436,851 | 3/1948 | Businger ............................. | 548/313 |
| 2,955,057 | 10/1960 | Gagliardi et al. .................... | 548/313 |
| 3,246,002 | 4/1966 | Gagliardi et al. .................... | 260/299 |
| 3,256,247 | 6/1966 | Gagliardi et al. .................... | 548/313 |
| 3,576,858 | 4/1971 | Mizoguchi et al. .................. | 548/313 |
| 3,798,233 | 3/1974 | Akiba et al. .......................... | 548/313 |
| 4,089,860 | 5/1978 | Merten et al. ........................ | 548/313 |

FOREIGN PATENT DOCUMENTS

| | | | |
|---|---|---|---|
| 2539730 | 3/1977 | Fed. Rep. of Germany ........... | 548/313 |
| 1273868 | 9/1961 | France .................................... | 548/313 |

OTHER PUBLICATIONS

Dakin, Amer. Chem. Journ. 1910, vol. 44, pp. 48–60.
Ware, Chem. Rev. 1950, vol. 46, pp. 406–407.

*Primary Examiner*—Natalie Trousof
*Assistant Examiner*—Natalia Harkaway
*Attorney, Agent, or Firm*—Jacobs & Jacobs

[57] ABSTRACT

A compound of formula (I)

$$\text{H-N} \underset{\underset{X}{\|}}{\overset{\overset{O}{\|}}{\diagdown}} \underset{N}{\diagup} \text{CH}(CH_2)_n CO_2 R_1 \quad N-CH_2-C(R_3)(R_2)(R_4) \quad (I)$$

wherein:
X is O or S;
n is 1 to 8;
$R_1$ is hydrogen, or $CO_2R_1$ represents an ester group in which the $R_1$ moiety contains from 1-12 carbon atoms;
$R_2$ is hydrogen, $C_{1-4}$ alkyl, or phenyl;
$R_3$ is hydroxy or protected hydroxy;
$R_4$ is hydrogen, $C_{1-9}$ alkyl, $C_{3-8}$ cycloalkyl, $C_{3-8}$ cycloalkyl-$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
$R_2$ and $R_4$ taken with the carbon atom to which they are joined represent a $C_{5-8}$ cycloalkyl group; and salts thereof; has useful pharmacological activity.

22 Claims, No Drawings

1-(3-HYDROXYALK-1-YL)-5-(CARBOXYALKYL)-HYDANTOIN DERIVATIVES

CROSS-REFERENCE TO RELATED APPLICATION

This is a continuation-in-part of Ser. No. 858,562 filed Dec. 8, 1977, now abandoned.

This invention relates to novel compounds having pharmacological activity, to a process for their preparation, to intermediates useful in that process and to pharmaceutical compositions containing them.

Offenlegungsschrift No. 2,323,193 discloses that pyrazolidine derivatives of the formula (I)′:

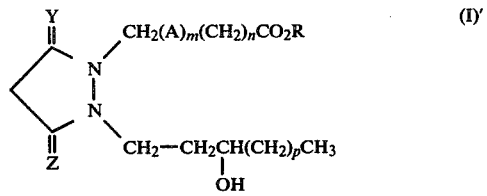

wherein A is CH=CH or C≡C; R is H, an alkali metal, an amine salt, or an ≯12C hydrocarbon or chlorohydrocarbon residue; m is 0 or 1; n is 0–6; p is 0–6; and Y and Z are O or $H_2$ except that Y and Z are not both O; have similar biological properties to the prostaglandins or are antagonists of prostaglandins.

French Patent Application No. 2,258,376 discloses that 10-aza prostaglandins of formula (II)″:

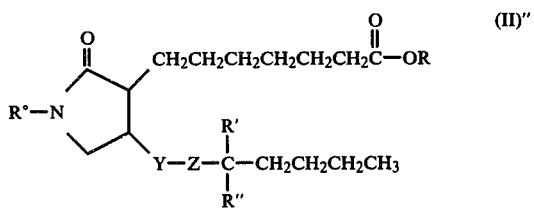

wherein R=H or lower alkyl; R′ and R″=$CH_3$ or $C_2H_5$; R°=H or lower alkyl; Y=—$CH_2CH_2$—, or —CH=CH—; Z=—CO or —CH(∼OH)—; are useful in the treatment of blood pressure and gastrointestinal disorders, and in the preparation for confinement.

Belgian Patent No. 835,989 discloses that compounds of the formula (III)″:

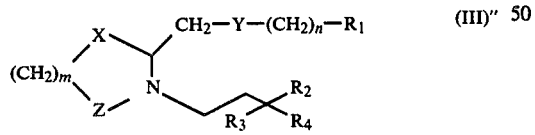

wherein:
X is CO, protected CO, CROH in which R is hydrogen or $C_{1-4}$ alkyl and in which the OH moiety may be protected; Y is $CH_2CH_2$ or CH=CH; Z is CO or $CH_2$; n is 1 to 8; m is 1, 2 or 3; $R_1$ is hydrogen, $CH_2OH$, $CH_2OH$ in which the OH moiety is protected, $CO_2W$ wherein W is hydrogen or $CO_2W$ represents an ester group in which the ester moiety contains from 1 to 12 carbon atoms, or $CONH_2$; $R_2$ is hydrogen, $C_{1-4}$ alkyl, or taken together with $R_3$ and the carbon atom to which it is attached represents a carbonyl group; $R_3$ is hydrogen, hydroxy or protected hydroxy; $R_4$ is hydrogen or $C_{1-9}$ alkyl; and salts thereof; have useful pharmacological activity.

A novel class of compounds also having useful pharmacological activity has now been discovered, which compounds are structurally distinct from the prior art referred to above.

Accordingly the present invention provides a compound of the formula (I):

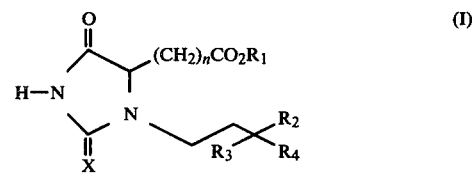

wherein:
X is O or S;
n is 1 to 8;
$R_1$ is hydrogen, or $CO_2R_1$ represents an ester group in which the $R_1$ moiety contains from 1–12 carbon atoms;
$R_2$ is hydrogen, $C_{1-4}$ alkyl, or phenyl;
$R_3$ is hydroxy or protected hydroxy;
$R_4$ is hydrogen, $C_{1-9}$ alkyl, $C_{3-8}$ cycloalkyl, $C_{3-8}$ cycloalkyl-$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
$R_2$ and $R_4$ taken with the carbon atom to which they are joined represent a $C_{5-8}$ cycloalkyl group; and salts thereof.

A group of compounds within formula (I) include those wherein:
X is O or S; n is 4 to 8;
$R_1$ is hydrogen, or $CO_2R_1$ represents an ester group in which the $R_1$ moiety contains from 1 to 12 carbon atoms;
$R_2$ is hydrogen, $C_{1-4}$ alkyl, or phenyl;
$R_3$ is hydroxy or protected hydroxy;
$R_4$ is hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl - $C_{1-6}$- alkyl, any of which phenyl or naphthyl moieties may be substituted by one or more halogen, trifluoromethyl, $C_{1-6}$ alkyl, $C_{1-6}$ alkoxy or nitro groups: and salts thereof.

Particularly suitable compounds within formula (I) include those where X is O.

Suitably n is 5, 6 or 7, preferably 6.

$R_1$ is hydrogen or $CO_2R_1$ represents an ester group in which the $R_1$ moiety contains from 1 to 12 carbon atoms. Examples of $R_1$ include hydrogen, methyl, ethyl, n- and iso-propyl, n-, sec- and tert-butyl, phenyl, benzyl, toluyl and the like, while normally hydrogen or $C_{1-6}$ alkyl groups are preferred.

Suitable examples of $R_2$ include hydrogen, methyl, ethyl and phenyl. More suitably $R_2$ is hydrogen, methyl or ethyl, preferably methyl.

Suitable protected hydroxyl groups $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl group or like groups. Preferably $R_3$ is hydroxyl.

Suitable groups $R_4$ when $R_4$ is an alkyl group include $C_{4-9}$ alkyl groups. Such $C_{4-9}$ alkyl groups may be straight chain alkyl groups, such n-butyl, n-pentyl, n-hexyl and n-heptyl, or may be alkyl groups branched by one or two methyl groups (at the same or different carbon atoms). Thus for example, $R_4$ may be a group $CH_2R_7$, $CH(CH_3)R_7$ of $C(CH_3)_2R_7$, wherein $R_7$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_7$ and $C(CH_3)_2R_7$ wherein $R_7$ is straight chain butyl, pentyl and hexyl.

Other suitable examples of $R_4$ when $R_4$ is an alkyl group include the lower alkyl groups, that is when $R_4$ is $C_{1-4}$ alkyl group.

When $R_4$ is or contains a $C_{3-8}$ cycloalkyl moiety, the moiety may be cyclopropyl. The moiety may also be a $C_{5-8}$ cycloalkyl moiety such as a cyclohexyl moiety. Examples of suitable $C_{1-6}$ alkyl moieties when $R_4$ is a $C_{3-8}$ cycloalkyl-$C_{1-6}$ alkyl group include methyl, ethyl, propyl, butyl and amyl.

When $R_4$ is an aryl group as previously defined, suitable groups $R_4$ include phenyl, phenylmethyl, phenylethyl, phenyl n-propyl, phenyl n-butyl, naphthyl, naphthyl-methyl, naphthyl-ethyl, naphthyl n-propyl and naphthyl n-butyl, and such groups branched in the alkyl moiety by one or two methyl groups (at the same or different carbon atoms). These groups may be substituted in the phenyl or naphthyl moiety by normally one, two or three groups selected from those substituent groups listed hereinbefore. Examples of suitable substituent groups include fluorine, chlorine and bromine atoms and $CF_3$, methyl, ethyl, n- and iso-propyl, methoxy and ethoxy, n- and iso-propoxy and nitro groups. Other examples of such groups include hydroxy and benzyloxy. Preferably the aryl moieties when substituted by such groups will be mono or di-substituted.

Also, $R_2$ and $R_4$ taken with the carbon atom to which they are joined can represent a $C_{5-8}$ cycloalkyl group, such as the cyclohexyl group.

The compounds of the formula (I) may form conventional salts. Such salts include those with alkali and alkaline earth metals, suitably sodium and potassium, and ammonium and substituted ammonium salts.

From the aforesaid it will be seen that one particularly suitable group of compounds within formula (I) is of formula (II):

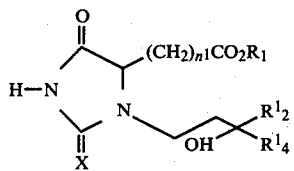

(II)

wherein:
$X_1$ and $R_1$ are as defined in formula (I):
$n^1$ is 5, 6 and 7;
$R^1_2$ is hydrogen, methyl, ethyl or phenyl;
$R^1_4$ is hydrogen or $C_{1-9}$ alkyl; and salts thereof.
In formula (II) $n^1$ is preferably 6. Also suitably X is O.

$R^1_2$ is more suitably hydrogen, methyl or ethyl, preferably methyl.

While $R^1_4$ may be hydrogen or a $C_{1-9}$ alkyl group, it is normally a $C_{4-9}$ alkyl group. In such cases suitable and preferred straight chain and branched groups $R^1_4$ include those previously described as suitable and preferred for the group $R_4$ when $R_4$ is a $C_{4-9}$ alkyl group. Such preferred groups $R^1_4$ include straight chain pentyl, hexyl and heptyl, and of these normally the most useful is straight chain hexyl. Other preferred groups $R^1_4$ include $CH(CH_3)R^1_7$ and $C(CH_3)_2R^1_7$ wherein $R^1_7$ is straight chain butyl, pentyl or hexyl.

A second group of compounds within formula (I) of particular interest are those of formula (III):

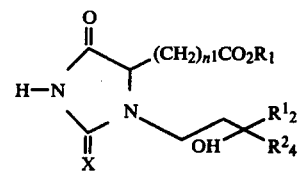

(III)

wherein:
$X_1$ and $R_1$ are as defined in formula (I);
$n^1$ is 5, 6 or 7;
$R^1_2$ is hydrogen, methyl, ethyl or phenyl;
$R^2_4$ is a group of formula (IV)

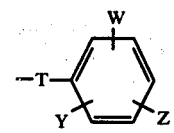

(IV)

wherein T is a bond, or a $C_{1-6}$ alkylene group which may be straight chain or branched by one or two methyl groups at the same or different carbon atoms; and W, Y and Z are each hydrogen or fluorine, chlorine or bromine atoms, or $CF_3$, methyl, ethyl, n- or iso-propyl, methoxy, ethoxy, n- or iso-propoxy or nitro groups; and salts thereof.

In formula (III) $n^1$ is preferably 6. Also suitably X is O.

$R^1_2$ is more suitably hydrogen, methyl or ethyl, preferably methyl.

In formula (IV) often T will be a group $-(CH_2)_q-$ wherein q is 0 to 4. Also, suitably W and Y are hydrogen.

Another group of compounds within formula (I) of particular interest is of formula (V):

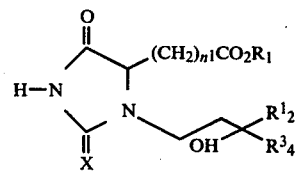

(V)

wherein:
$X_1$ and $R_1$ are as defined in formula (I);
$n^1$ is 5, 6 or 7;
$R^1_2$ is hydrogen, methyl, ethyl or phenyl;
$R^3_4$ is a group of formula (VI):

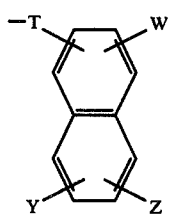
(VI)

wherein T, W, Y and Z are as defined in formula (IV); and salts thereof.

In formula (V) $n^1$ is preferably 6. Also suitably X is O. $R^1_2$ is more suitably hydrogen, methyl or ethyl, preferably methyl.

In formula (VI) often T will be a group $-(CH_2)_q-$ wherein q is 0 to 4. Also suitably W and Y are hydrogen.

A further group of compounds within formula (I) of interest are of formula (VII):

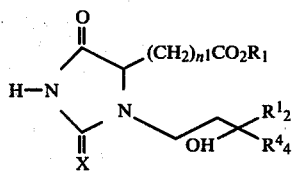
(VII)

wherein:
$X_1$ and $R_1$ are as defined in formula (I);
$n^1$ is 5, 6 or 7;
$R^1_2$ is hydrogen, methyl, ethyl, or phenyl;
$R^4_4$ is a group of formula (VIII):

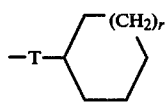
(VIII)

wherein T is as defined in formula (IV) and r is 0 to 3; and salts thereof.

In formula (VII) $n^1$ is preferably 6. Also suitably X is O.

$R^1_2$ is more suitably hydrogen, methyl, or ethyl, preferably methyl.

In formula (VIII) often T will be a group $-(CH_2)_q-$ wherein q is 0 to 4. Also suitably r is 1.

The present invention further provides a process for the preparation of the compounds of the formula (I), which process comprises the cyclisation of a compound of formula (IX):

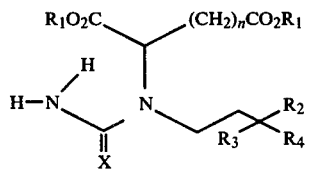
(IX)

wherein the variable groups are as defined; and thereafter if desired or necessary converting $R_1$ and/or $R_3$ in the thus formed compound into other variables $R_1$ and $R_3$.

When $R_1$ is hydrogen in the compound of formula (IX), then the cyclisation may suitably be carried out in aqueous conditions at acid pH, for example in 25% aqueous acid. Such compounds of the formula (IX) can be prepared by reacting a salt $M^+C^-NX$, wherein $M^+$ is a metal ion and X is O or S as defined, with a compound of formula (X):

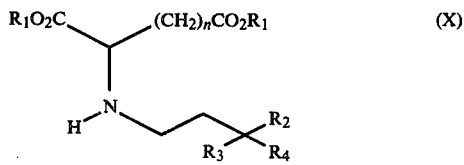
(X)

wherein n, $R_1$, $R_2$, $R_3$ and $R_4$ are as defined. The metal salt thus obtained can be converted to the acid (IX) with mineral acid. Suitable $M^+$ is a sodium or potassium ion, preferably a potassium ion.

When $R_1$ is other than hydrogen, the compound of the formula (IX) is conveniently formed in situ during the conversion of a compound of formula (X) into a corresponding compound of the formula (I) by reaction with $M^+C^-NX$, a preferred process of the invention. This conversion may suitably be achieved using a hydrochloride salt of the compound of the formula (X) and reacting the salt in aqueous solution at reflux or in aqueous dichloromethane with a phase transfer catalyst.

The conversion of a compound of the formula (I) to another compound of the formula (I) wherein $R_1$ and/or $R_3$ are altered, when desired or necessary, may be achieved in conventional manner.

For example, if desired the group $R_1$ in the compound may be varied by conventional esterification and/or de-esterification reactions. Similarly protected $R_3$ hydroxy moieties may be deprotected in conventional manner. For example when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I). Also when a compound of the formula (I) contains an acidic hydrogen atom(s), salts thereof may be prepared in conventional manner for example by reacting the compound of the formula (I) with the required base. For salts at 3-hydrogen, the base should be a strong base such as for example sodium in an alcohol, such as ethanol, or the like.

It is believed that the compounds of formula (IX) are novel, and thus they form an important part of this invention as intermediates.

The compounds of the formula (X) may be prepared by the method disclosed in Belgian Pat. No. 835,989, or by analogous methods thereto.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

Compounds within the formula (I) have useful pharmacological activity. For example compounds within the formula (I) have anti-gastric secretion activity e.g. anti-ulcer activity, cardiovascular activity e.g. anti-hypertensive activity, platelet aggregation inhibition activity, affect the respiratory tract e.g. bronchodilator activity, and have anti-fertility, smooth muscle and anti-arrythmic activity.

In general it may be said that compound within the formula (I) have a range of pharmacological activities similar to those shown by the natural prostaglandins, but that these activities tend to be rather more selective.

The invention thereof also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may be in unit does presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described idsorders will depend on the actual compound of the formula (I) used, and also on other factors such as the seriousness of the disorder being treated.

The invention also provides a method of treatment and/or propylaxis of disorders in human beings or animals which comprises the administration to the sufferer of an effective amount of a compound of the formula (I).

Normally, however the compounds will be used in the therapy of human disorders.

The following Example illustrates the preparation of a compound of the formula (I):

EXAMPLE 1

Compound 1

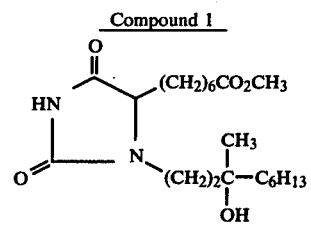

Dry hydrogen chloride gas was passed into an ice-cold solution of dimethyl 2-[N-(3'-hydroxy-3'-methyl)-n-nonyl]aminoazelate (40 g) in dry ether (1 l). The ether was evaporated in vacuo and the resulting hydrochloride was stirred with water (300 ml). A solution of potassium cyanate (8.2 g; 1.01 eq) in water (20 ml) was added and the resulting suspension was stirred at room temperature for 1.5 hours then at reflux for 1.5 hours. The mixture was allowed to cool and the product was extracted into dichloramethane. The dichloromethane solution was washed with brine until the washings were neutral then was dried and evaporated to give a yellow gum (38 g). A sample was purified via column chromatography (silica gel; 30:1) using chloroform, and chloroform methanol mixtures as eluants to give 1-(3'-hydroxy-3'-methyl-n-nonyl)-5-(6"-methoxycarbonyl-n-hexyl) hydantoin as a pale yellow gum.

| ANALYTICAL DATA | | |
|---|---|---|
| Compound C1 | | |
| I.R. (cm$^{-1}$) | : | 3500, [OH]; 3300, [NH]; |
| | | 1770, 1710, [—N—C—N—C—]; $\overset{\|}{O}$ $\overset{\|}{O}$ |
| | | 1730, [OCO$_2$CH$_3$]. |
| NMR ( ) | : | 7.85, (m), [ CH$_2$CO$_2$CH$_3$], |
| | | 7.5 to 6.5, (m), [—N—CH$_2$]; 6.4, (s), [—CO$_2$CH$_3$] |
| | | 5.95, (broad s), [—N—CH]. |
| Mass Spec requires found | : : | C$_{21}$H$_{36}$N$_2$O$_4$ (m*·H$_2$O) 380.2675 380.2659 |

We claim:
1. A compound of the formula:

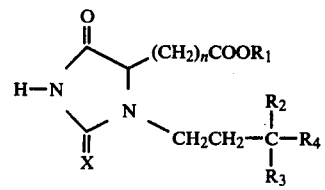

or a pharmaceutically acceptable salt thereof, wherein
X is O or S;
n has a value of from 1 to 8;
R$_1$ is hydrogen; alkyl; phenyl or aralkyl of up to 12 carbon atoms;
R$_2$ when taken alone is hydrogen; alkyl of 1 to 4 carbon atoms; or phenyl;
R$_3$ is hydroxy; alkanoyloxy of 1 to 4 carbon atoms or benzyloxy;

R$_4$ when taken alone is hydrogen; alkyl of 1 to 9 carbon atoms; cycloalkyl of 3 to 8 carbon atoms; phenyl; naphthyl; or alkyl of 1 to 6 carbon atoms substituted with phenyl, naphthyl or cycloalkyl of 3 to 8 carbon atoms; any of said phenyl rings and said naphthyl rings being unsubstituted or substituted with halo, trifluoromethyl, alkyl of 1 to 6 carbon atoms, hydroxy, alkoxy of 1 to 6 carbon atoms, phenylalkoxy wherein alkoxy contains from 1 to 6 carbon atoms or nitro; and R$_2$ and R$_4$ when taken together, together with the carbon atom to which they are joined, are cycloalkylidene of 5 to 8 carbon atoms.

2. A compound according to claim 1 wherein X is O.

3. A compound according to claim 1 wherein n is 5, 6 or 7.

4. A compound according to claim 1 wherein R$_1$ is hydrogen or alkyl of 1 to 6 carbon atoms.

5. A compound according to claim 1 wherein R$_2$ is hydrogen or methyl.

6. A compound according to claim 1 wherein R$_3$ is hydroxy.

7. A compound according to claim 1 wherein R$_4$ is alkyl of 1 to 9 carbon atoms.

8. A compound according to claim 1 wherein:
X is O or S;
n has a value of 4 to 8;
R$_1$ is hydrogen, alkyl or aralkyl of up to 12 carbon atoms;
R$_2$ is hydrogen, alkyl of 1 to 4 carbon atoms, or phenyl;
R$_3$ is hydroxy; alkanoyloxy of 1 to 4 carbon atoms or benzyloxy;
R$_4$ is hydrogen, alkyl of 1 to 9 carbon atoms, cycloalkyl of 5 to 8 carbon atoms, phenyl, naphthyl, alkyl of 1 to 6 carbon atoms substituted with phenyl, naphthyl or cycloalkyl of 5 to 8 carbon atoms, any of said phenyl rings or naphthyl rings being unsubstituted or substituted with halo, trifluoromethyl, alkyl of 1 to 6 carbon atoms, alkoxy of 1 to 6 carbon atoms or nitro.

9. A compound according to claim 8 wherein n is 5, 6 or 7.

10. A compound according to claim 8 wherein R$_3$ is hydroxy.

11. A compound according to claim 8 wherein R$_4$ is alkyl of 1 to 9 carbon atoms.

12. A compound according to claim 8 wherein: n is 5, 6 or 7; R$_2$ is hydrogen, methyl, ethyl or phenyl; R$_3$ is hydroxy; R$_4$ is hydrogen or alkyl of 1 to 9 carbon atoms.

13. A compound according to claim 12 wherein X is O.

14. A compound according to claim 12 wherein R$_1$ is hydrogen or alkyl of 1 to 6 carbon atoms.

15. A compound according to claim 12 wherein R$_2$ is hydrogen.

16. A compound according to claim 12 wherein R$_2$ is methyl.

17. A compound according to claim 12 wherein R$_4$ is alkyl of 4 to 9 carbon atoms.

18. A compound according to claim 17 wherein R$_4$ is n-pentyl, n-hexyl or n-heptyl.

19. A compound according to claim 18 wherein R$_4$ is n-hexyl.

20. A compound according to claim 17 wherein R$_4$ is hex-2-yl, hept-2-yl or oct-2-yl.

21. A pharmaceutical composition for effecting a prostaglandin-like response comprising an effective amount of a compound according to claim 1 and a pharmaceutically acceptable carrier.

22. The method of effecting a prostaglandin-like response in humans and other animals which comprises administering thereto an effective amount of a compound according to claim 1.

* * * * *

Notice of Adverse Decision in Interference

In Interference No. 100,772, involving Patent No. 4,152,445, G. Wootton, 1-(3-HYDROXYALK-1-YL)-5-(CARBOXYALKYL) HYDANTOIN DERIVATIVES, final judgment adverse to the patentee was rendered Mar. 22, 1983, as to claims 1–22.

*[Official Gazette June 14, 1983.]*